United States Patent
Donahue et al.

(10) Patent No.: US 10,422,008 B2
(45) Date of Patent: Sep. 24, 2019

(54) DISCRIMINATING BRAF MUTATIONS

(71) Applicant: Quest Diagnostics Investments Incorporated, Wilmington, DE (US)

(72) Inventors: Amber C. Donahue, Rancho Santa Margarita, CA (US); Yen-lin Peng, Mission Viejo, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 67 days.

(21) Appl. No.: 15/120,345

(22) PCT Filed: Feb. 20, 2015

(86) PCT No.: PCT/US2015/016759
§ 371 (c)(1),
(2) Date: Aug. 19, 2016

(87) PCT Pub. No.: WO2015/127168
PCT Pub. Date: Aug. 27, 2015

(65) Prior Publication Data
US 2017/0175198 A1   Jun. 22, 2017

Related U.S. Application Data

(60) Provisional application No. 61/943,577, filed on Feb. 24, 2014.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2012/0252015 A1 * 10/2012 Hindson .............. C12Q 1/6883
435/6.11
2013/0296176 A1    11/2013 Marziali et al.

OTHER PUBLICATIONS

Weisbart, R.H. et al. Journal of Biological Chemistry 285(45):34299 (Nov. 2010).*
Panka, D.J. et al. Author manuscript of Melanoma Research 20(5):401 (Oct. 2011).*
El-Osta, H. et al. PLoS One 6(10):e25806 (Oct. 2011).*
Jarry, A. et al. Molecular and Cellular Probes 18:349 (2004).*
Nomura, N. et al. Tissue Antigens 38:53 (1991).*
Panka et al., "An inexpensive, specific and highly sensitive protocol to detect the BrafV600E mutation in melanoma tumor biopsies and blood," Melanoma Res., vol. 20, No. 5, pp. 401-407, Oct. 2010.
International Search Report dated Jul. 10, 2015 in application No. PCT/US2015/16759.

* cited by examiner

*Primary Examiner* — Diana B Johannsen
(74) *Attorney, Agent, or Firm* — Foley & Lardner LLP (57) ABSTRACT

Provided herein are methods for detecting and discriminating BRAF V600 mutations. Also provided herein are methods for diagnosis, prognosis, management, and treatment decisions of BRAF V600 mutation-related diseases or conditions.

13 Claims, 3 Drawing Sheets
Specification includes a Sequence Listing.

Discrimination of V600E and V600K Mutants

SfcI: CTRYAG (R=A/G; Y=C/T) (cut after C)

WT: 5'-gtctagctacagTgaaatctcgatggagtg-3'

V600E: 5'-gtctagctacagAgaaatctcgatggagtg-3'

V600K: 5'-gtctagctacaAAgaaatctcgatggagtg-3'

SfcI cuts WT and V600E amplicon but not V600K mutants.

ASO=allele-specific PCR for V600E(&K)   Ref=reference PCR for total BRAF

FIGURE 1

```
   1 cgcctcccct tccccctcccc gcccgacagc ggccgctcgg gccccggctc tcggttataa
  61 gatggcggcg ctgagcggtg gcggtggtgg cggcgcggag ccgggccagg ctctgttcaa
 121 cggggacatg gagcccgagg ccggcgccgg cgccggcgcc gcggcctctt cggctgcgga
 181 ccctgccatt ccggaggagg tgtggaatat caaacaaatg attaagttga cacaggaaca
 241 tatagaggcc ctattggaca aatttggtgg ggagcataat ccaccatcaa tatatctgga
 301 ggcctatgaa gaatacacca gcaagctaga tgcactccaa caaagagaac aacagttatt
 361 ggaatctctg gggaacggaa ctgattttc tgtttctagc tctgcatcaa tggataccgt
 421 tacatcttct tcctcttcta gcctttcagt gctaccttca tctctttcag tttttcaaaa
 481 tcccacagat gtggcacgga gcaaccccaa gtcaccacaa aaacctatcg ttagagtctt
 541 cctgcccaac aaacagagga cagtggtacc tgcaaggtgt ggagttacag tccgagacag
 601 tctaaagaaa gcactgatga tgagaggtct aatcccagag tgctgtgctg tttacagaat
 661 tcaggatgga gagaagaaac caattggttg ggacactgat atttcctggc ttactggaga
 721 agaattgcat gtggaagtgt tggagaatgt tccacttaca acacacaact ttgtacgaaa
 781 aacgtttttc accttagcat tttgtgactt ttgtcgaaag ctgcttttcc agggtttccg
 841 ctgtcaaaca tgtggttata aatttcacca gcgttgtagt acagaagttc cactgatgtg
 901 tgttaattat gaccaacttg atttgctgtt tgtctccaag ttctttgaac accacccaat
 961 accacaggaa gaggcgtcct tagcagagac tgccctaaca tctggatcat ccccttccgc
1021 acccgcctcg gactctattg ggccccaaat tctcaccagt ccgtctcctt caaaatccat
1081 tccaattcca cagcccttcc gaccagcaga tgaagatcat cgaaatcaat ttgggcaacg
1141 agaccgatcc tcatcagctc ccaatgtgca tataaacaca atagaacctg tcaatattga
1201 tgacttgatt agagaccaag gatttcgtgg tgatggagga tcaaccacag gtttgtctgc
1261 taccccccct gcctcattac ctggctcact aactaacgtg aaagccttac agaaatctcc
1321 aggacctcag cgagaaagga agtcatcttc atcctcagaa gacaggaatc gaatgaaaac
1381 acttggtaga cgggactcga gtgatgattg ggagattcct gatgggcaga ttacagtggg
1441 acaaagaatt ggatctggat catttggaac agtctacaag ggaaagtggc atggtgatgt
1501 ggcagtgaaa atgttgaatg tgacagcacc tacacctcag cagttacaag ccttcaaaaa
1561 tgaagtagga gtactcagga aaacacgaca tgtgaatatc ctactcttca tgggctattc
1621 cacaaagcca caactggcta ttgttaccca gtggtgtgag ggctccagct tgtatcacca
1681 tctccatatc attgagacca aatttgagat gatcaaactt atagatattg cacgacagac
1741 tgcacagggc atggattact tacacgccaa gtcaatcatc cacagagacc tcaagagtaa
1801 taatatattt cttcatgaag acctcacagt aaaaataggt gattttggtc tagctacagt
1861 gaaatctcga tggagtgggt cccatcagtt tgaacagttg tctggatcca ttttgtggat
1921 ggcaccagaa gtcatcagaa tgcaagataa aaatccatac agctttcagt cagatgtata
1981 tgcatttgga attgttctgt atgaattgat gactggacag ttaccttatt caaacatcaa
2041 caacagggac cagataattt ttatggtggg acgaggatac ctgtctccag atctcagtaa
2101 ggtacggagt aactgtccaa aagccatgaa gagattaatg gcagagtgcc tcaaaaagaa
2161 aagagatgag agaccactct ttcccccaaat tctcgcctct attgagctgc tggcccgctc
2221 attgccaaaa attcaccgca gtgcatcaga accctccttg aatcgggctg gtttccaaac
2281 agaggatttt agtctatatg cttgtgcttc tccaaaaaca cccatccagg caggggata
2341 tggtgcgttt cctgtccact gaaacaaatg agtgagagag ttcaggagag tagcaacaaa
2401 aggaaaataa atgaacatat gtttgcttat atgttaaatt gaataaaata ctctcttttt
2461 ttttaaggtg aaccaaagaa cacttgtgtg gttaaagact agatataatt ttccccaaa
2521 ctaaaattta tacttaacat tggattttta acatccaagg gttaaaatac atagacattg
2581 ctaaaaattg gcagagcctc ttctagaggc tttactttct gttccgggtt tgtatcattc
2641 acttggttat tttaagtagt aaacttcagt ttctcatgca acttttgttg ccagctatca
2701 catgtccact agggactcca gaagaagacc ctacctatgc ctgtgtttgc aggtgagaag
2761 ttggcagtcg gttagcctgg gttagataag gcaaactgaa cagatctaat ttaggaagtc
2821 agtagaattt aataattcta ttattattct taataatttt tctataacta tttcttttta
2881 taacaatttg gaaaatgtgg atgtctttta tttccttgaa gcaataaact aagtttcttt
2941 ttataaaaa
```

FIGURE 2

```
  1 maalsggggg gaepgqalfn gdmepeagag agaaassaad paipeevwni kqmikltqeh
 61 iealldkfgg ehnppsiyle ayeeytskld alqqreqqll eslgngtdfs vsssasmdtv
121 tsssssslsv lpsslsvfqn ptdvarsnpk spqkpivrvf lpnkqrtvvp arcgvtvrds
181 lkkalmmrgl ipeccavyri qdgekkpigw dtdiswltge elhvevlenv pltthnfvrk
241 tfftlafcdf crkllfqgfr cqtcgykfhq rcstevplmc vnydqldllf vskffehhpi
301 pqeeaslaet altsgsspsa pasdsigpqi ltspspsksi pipqpfrpad edhrnqfgqr
361 drsssapnvh intiepvnid dlirdqgfrg dggsttglsa tppaslpgsl tnvkalqksp
421 gpqrerksss ssedrnrmkt lgrrdssddw eipdgqitvg qrigsgsfgt vykgkwhgdv
481 avkmlnvtap tpqqlqafkn evgvlrktrh vnillfmgys tkpqlaivtq wcegsslyhh
541 lhiietkfem iklidiarqt aqgmdylhak siihrdlksn niflhedltv kigdfglatv
601 ksrwsgshqf eqlsgsilwm apevirmqdk npysfqsdvy afgivlyelm tgqlpysnin
661 nrdqiifmvg rgylspdlsk vrsncpkamk rlmaeclkkk rderplfpqi lasiellars
721 lpkihrsase pslnragfqt edfslyacas pktpiqaggy gafpvh
```

FIGURE 3

Discrimination of V600E and V600K Mutants

ASO=allele-specific PCR for V600E(&K)   Ref=reference PCR for total BRAF

SEQUENCE LISTING

```
<160> NUMBER OF SEQ ID NOS: 5

<210> SEQ ID NO 1
<211> LENGTH: 2949
<212> TYPE: DNA
<213> ORGANISM: Homo sapiens

<400> SEQUENCE: 1
cgcctcccct ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgatttttc tgtttctagc tctgcatcaa tggataccgt     420
tacatcttct tcctcttcta gcctttcagt gctaccttca tctctttcag tttttcaaaa     480
tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg ggacactgat atttcctggc ttactggaga     720
agaattgcat gtggaagtgt tggagaatgt tccacttaca acacacaact ttgtacgaaa     780
aacgtttttc accttagcat tttgtgactt ttgtcgaaag ctgcttttcc agggtttccg     840
```

```
ctgtcaaaca tgtggttata aatttcacca gcgttgtagt acagaagttc cactgatgtg      900
tgttaattat gaccaacttg atttgctgtt tgtctccaag ttctttgaac accacccaat      960
accacaggaa gaggcgtcct tagcagagac tgccctaaca tctggatcat cccctttccgc    1020 acccgcctcg gactctattg gcccccaaat tctcaccagt ccgtctcctt caaaatccat    1080
tccaattcca cagcccttcc gaccagcaga tgaagatcat cgaaatcaat ttgggcaacg    1140
agaccgatcc tcatcagctc ccaatgtgca tataaacaca atagaacctg tcaatattga    1200
tgacttgatt agagaccaag gatttcgtgg tgatggagga tcaaccacag gtttgtctgc    1260 tacccccccct gcctcattac ctggctcact aactaacgtg aaagccttac agaaatctcc    1320
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta tgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct tcccccaaat tctcgcctct attgagctgc tggcccgctc    2220
attgccaaaa attcaccgca gtgcatcaga ccctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggatttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca actttgttg ccagctatca    2700 catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttctttta    2880 taacaatttg gaaaatgtgg atgtcttta tttccttgaa gcaataaact aagtttcttt    2940
ttataaaaa                                                            2949
```

<210> SEQ ID NO 2
<211> LENGTH: 766
<212> TYPE: PRT
<213> ORGANISM: Homo sapiens

<400> SEQUENCE: 2

```
Met Ala Ala Leu Ser Gly Gly Gly Gly Ala Glu Pro Gly Gln
 1               5                  10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415
```

```
Gln Lys Ser Pro Gly Pro Gln Arg Glu Arg Lys Ser Ser Ser Ser
            420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
            485                 490                 495
Ala Phe Lys Asn Glu Val Gly Val Leu Arg Lys Thr Arg His Val Asn
            500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
            530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
            565                 570                 575
Leu Lys Ser Asn Asn Ile Phe Leu His Glu Asp Leu Thr Val Lys Ile
            580                 585                 590
Gly Asp Phe Gly Leu Ala Thr Val Lys Ser Arg Trp Ser Gly Ser His
            595                 600                 605
Gln Phe Glu Gln Leu Ser Gly Ser Ile Leu Trp Met Ala Pro Glu Val
            610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
            645                 650                 655
Ser Asn Ile Asn Asn Arg Asp Gln Ile Ile Phe Met Val Gly Arg Gly
            660                 665                 670
Tyr Leu Ser Pro Asp Leu Ser Lys Val Arg Ser Asn Cys Pro Lys Ala
            675                 680                 685
Met Lys Arg Leu Met Ala Glu Cys Leu Lys Lys Lys Arg Asp Glu Arg
            690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
            725                 730                 735
Gly Phe Gln Thr Glu Asp Phe Ser Leu Tyr Ala Cys Ala Ser Pro Lys
            740                 745                 750
Thr Pro Ile Gln Ala Gly Gly Tyr Gly Ala Phe Pro Val His
            755                 760                 765

<210> SEQ ID NO 3
<211> LENGTH: 30
<212> TYPE: DNA
<213> ORGANISM: Homo sapiens

<400> SEQUENCE: 3
gtctagctac agtgaaatct cgatggagtg                                      30

<210> SEQ ID NO 4
```

```
<211> LENGTH: 30
<212> TYPE: DNA
<213> ORGANISM: Homo sapiens

<400> SEQUENCE: 4
gtctagctac agagaaatct cgatggagtg                                              30

<210> SEQ ID NO 5
<211> LENGTH: 30
<212> TYPE: DNA
<213> ORGANISM: Homo sapiens

<400> SEQUENCE: 5
gtctagctac aaagaaatct cgatggagtg                                              30
```

DISCRIMINATING BRAF MUTATIONS

CROSS-REFERENCE TO RELATED APPLICATIONS

This application claims the benefit of U.S. Provisional Application No. 61/943,577, filed Feb. 24, 2014, the entire disclosure of which is herein incorporated by reference in its entirety.

FIELD OF THE INVENTION

Provided herein are methods for detecting and discriminating BRAF V600 mutations. Provided herein are also methods for diagnosis, prognosis, management, and treatment decisions in patients with BRAF V600 mutation-related diseases or conditions.

BACKGROUND OF THE INVENTION

BRAF ("v-raf murine sarcoma viral oncogene homolog B1") belongs to a family of serine-threonine protein kinases and plays a critical role in the mitogen-activated protein kinase/extracellular signal-regulated kinase (MAPK/ERK) signaling pathway. Mutations in BRAF are associated with multiple cancers, including colorectal cancer (CRC), thyroid cancer, non-small cell lung cancer (NSCLC), melanomas, and adenocarcinomas (Davies H, et al. Nature 2002; 417: 949-54; Rajagopalan H, et al., Nature 2002; 418:934.). BRAF is mutated in over 50% of melanomas, approximately 45% of thyroid cancers, and approximately 10% of colorectal cancers. BRAF mutations are also associated with LEOPARD syndrome, a developmental disorder with an increased incidence of multiple granular cell tumors.

The most prevalent BRAF mutation is a single amino acid substitution at position 600 of the BRAF protein, which is a valine in the wild-type molecule (V600). The most common BRAF V600 mutation is a glutamic acid substitution (V600E), comprising approximately 80-90% of all V600 mutations. The V600E mutation is caused by a T to A transversion in exon 15 of the BRAF gene, at nucleotide 1799 of the coding sequence given by NCBI Accession number NM_004333.4 (1799 T>A). The V600E mutation has been observed in over half of all microsatellite-unstable carcinomas and in a subset of stable colon tumors (Wang L, et al., Cancer Res 2003; 63:5209-12).

The V600E BRAF mutation is also frequently found in tumors of the nervous system, thyroid, skin, gastrointestinal tract, large intestine, biliary tract, ovary, eye, prostate, central nervous system, liver, small intestine, breast, pancreas, soft tissue, digestive tract, adrenal gland, autonomic ganglia, hematopoietic and lymphoid tissue, lung, esophagus, pituitary, and stomach.

The second most common BRAF V600 mutation is a lysine substitution (V600K), which is caused by a GT to AA transversion at nucleotides 1798-1799 of the BRAF coding sequence given by NCBI Accession number NM_004333.4 (1798-1799 GT>AA). Other V600 mutations include, but are not limited to, glutamine (V600R), aspartic acid (V600D), alanine (V600A), and methionine (V600M) substitutions.

Patients harboring BRAF V600K mutations have been shown to respond better to the BRAF inhibitor vemurafenib than to dacarbazine chemotherapy. Likewise, patients harboring BRAF V600E or V600K mutations have been shown to respond better to the mitogen-activated protein kinases kinase (MEK) inhibitor trametinib than to dacarbazine or paclitaxel chemotherapy.

Studies have shown that BRAF mutations are associated with enhanced and selective sensitivity to MEK inhibition compared to wild-type cells and cells harboring a RAS mutation. The effect is observed in BRAF mutant cells regardless of tissue lineage, and correlates with both down regulation of cyclin D1 expression and the induction of G1 arrest. Pharmacological MEK inhibition completely abrogates tumor growth in BRAF mutant xenografts (Solit, D. et al., Nature 2006; 439:358-362). These data suggest a dependency on MEK activity in BRAF mutant tumors, and point to a potential therapeutic strategy for this genetically defined tumor subtype.

A recent study reported the presence of the BRAF gain-of-function mutation V600R in synovial fibroblasts from rheumatoid arthritis patients, and demonstrated that BRAF-specific siRNA inhibits proliferation of the mutant fibroblasts. These findings suggest a mechanism for the fibroblast transformation associated with this condition, as well as a new target for therapeutic intervention (Weisbart, R. H. et al., 2010; 285(45): 34299-34303).

Roche has developed Cobas® 4800 BRAF V600 Mutation Test, which is a companion diagnostic for determining patient eligibility for Zelboraf (or vemurafenib) treatment. Zelboraf was approved by the FDA for the treatment of BRAF V600E mutation-positive inoperable or metastatic melanoma. The Cobas® test detects not only the V600E mutation, but also other V600 mutations such as V600K and V600D.

Several other methods known in the art may be used to detect BRAF V600 mutations, such as Sanger sequencing, which is currently used in clinical settings. A recent study comparing the sensitivity of the Cobas® 4800 BRAF V600 Mutation Test with Sanger sequencing found that the Cobas® test was less sensitive and less specific in detecting V600 mutations than Sanger sequencing (Qu et al., Journal of Molecular Diagnostics 2013; 15(6): 790-795). These findings indicate that the Cobas® assay can miss many V600 mutations in clinical specimens, and that additional assays are required to confirm negative Cobas® results.

Few advances have been made in protocols designed to evaluate patients with BRAF mutations such as V600E and V600K. Identifying specific BRAF mutations will help physicians determine the best treatment strategies and maximize the number of patients who can benefit from treatment with BRAF inhibitors, such as Zelboraf.

SUMMARY

In certain embodiments, provided herein is a method for identifying a specific mutation in the BRAF gene, which comprises: (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion. In some embodiments, the amplicon comprises the BRAF V600E mutation (1799T>A). In some embodiments, the amplicon comprises the BRAF V600K mutation (1798_1799GT>AA). In some embodiments, the amplicon does not comprise the wild type BRAF gene. In some embodiments, the restriction enzyme recognizes a 6-base motif that matches the sequence of the BRAF gene immediately upstream of the thymidine (T) to adenosine (A) mutation at position 1799 of the BRAF gene. In some embodiments, the restriction enzyme digests the BRAF V600E mutation (1799T>A) and the wild type BRAF gene, but not the BRAF V600K mutation (1798_1799GT>AA).

In some embodiments, the sample DNA is extracted from the plasma of an individual. In some embodiments, the individual is a melanoma patient.

In some embodiments, the incubation for the restriction enzyme digestion is for about one hour incubation at about 37° C. In some embodiments, the restriction enzyme is SfcI. In some embodiments, the presence or absence of a digestion can be detected by size separation. In some embodiments, the size separation is through denaturing HPLC. In other embodiments, the size separation is through capillary electrophoresis. In some embodiments, the capillary electrophoresis comprises utilizing a fluorophore-conjugated primer in the PCR amplification.

In some embodiments, provided herein is a method for diagnosing an individual with BRAF-related disease or condition by determining if the individual has a specific mutation in the BRAF gene associated with BRAF-related disease or condition comprising (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion, wherein the restriction enzyme digests the BRAF V600E mutation (1799T>A) and the wild type BRAF gene, but not the BRAF V600K mutation (1798_1799GT>AA).

In some embodiments, provided herein is a method for prognosis of an individual diagnosed with BRAF-related disease or condition by determining if the individual has a specific mutation in the BRAF gene associated with BRAF-related disease or condition comprising (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion, wherein the restriction enzyme digests the BRAF V600E mutation (1799T>A) and the wild type BRAF gene, but not the BRAF V600K mutation (1798_1799GT>AA).

In some embodiments, provided herein is a method for drug sensitivity of an individual diagnosed with BRAF-related disease or condition by determining if the individual has a specific mutation in the BRAF gene associated with BRAF-related disease or condition comprising (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion, wherein the restriction enzyme digests the BRAF V600E mutation (1799T>A) and the wild type BRAF gene, but not the BRAF V600K mutation (1798_1799GT>AA).

In some embodiments, provided herein is a method for guiding treatment decisions of an individual diagnosed with BRAF-related disease or condition by determining if the individual has a specific mutation in the BRAF gene associated with BRAF-related disease or condition comprising (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion, wherein the restriction enzyme digests the BRAF V600E mutation (1799T>A) and the wild type BRAF gene, but not the BRAF V600K mutation (1798_1799GT>AA).

In some embodiments, provided herein is a method for monitoring effectiveness of treatment of an individual diagnosed with BRAF-related disease or condition by determining if the individual has a specific mutation in the BRAF gene associated with BRAF-related disease or condition comprising (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion, wherein the restriction enzyme digests the BRAF V600E mutation (1799T>A) and the wild type BRAF gene, but not the BRAF V600K mutation (1798_1799GT>AA).

In some embodiments, provided herein is a kit useful for detecting a specific mutation in the BRAF gene in a sample DNA from an individual, said kit comprising (a) amplifying the sample DNA by PCR utilizing a forward primer and a reverse primer, wherein the forward primer and the reverse primer are configured to amplify DNA sequences containing a thymidine (T) to adenosine (A) mutation at position 1799 of the BRAF gene, but not the wild type BRAF gene, and (b) subjecting the amplicon to a restriction enzyme digestion, wherein the restriction enzyme digests the BRAF V600E mutation (1799T>A) and the wild type BRAF gene, but not the BRAF V600K mutation (1798_1799GT>AA).

In some embodiments, a sensitive quantitative PCR (qPCR) assay is designed and optimized to detect the most common BRAF V600E mutation (1799T>A) present in circulating DNA extracted from the plasma of melanoma patients. The nature of the assay design would also amplify V600K mutations (1798_1799GT>AA). Some studies have accepted the inclusion of some percentage of V600K mutants in the pool of V600E mutant patients due to a lack of specificity in the detection assay, including the study performed for FDA submission of the Roche cobas 4800 BRAF V600 Mutation Test as a companion diagnostic for the melanoma drug vemurafenib. Provided herein are methods that distinguish between BRAF V600E and V600K mutations, in the event that further studies someday demonstrated differential phenotypes or drug responsiveness for the two mutations.

In some embodiments, single or multiple mutant sequences can be assayed. Amplification of multiple mutant sequences can be performed simultaneously in a single reaction vessel, e.g., multiplex PCR. In this case, probes may be distinguishably labeled and/or amplicons may be distinguishable by size differentiation. Alternatively, the assay could be performed in parallel in separate reaction vessels. In such later case, the probes could have the same label.

In some embodiments, the methods further comprise a nucleic acid extraction step. Various extraction nucleic acid methods are known in the art which can be employed with the methods and compositions provided herein such as lysis methods (such as alkaline lysis), phenol:chloroform and isopropanol precipitation. Nucleic acid extraction kits can also be used. The extraction method can be, but not limited to, Agencourt Genfind™, Roche Cobas® or phenol:chloroform extraction using Eppendorf Phase Lock Gels®.

In some embodiments, at least one primer of each primer pair in the amplification reaction is labeled with a detectable moiety. Following amplification, the various target segments can be identified by size and color. The detectable moiety is preferably a fluorescent dye. In some embodiments, different pairs of primers in a multiplex PCR may be labeled with different distinguishable detectable moieties. Thus, for example, HEX and FAM fluorescent dyes may be present on different primers in multiplex PCR and associated with the resulting amplicons. In other embodiments, the forward primer is be labeled with one detectable moiety, while the reverse primer is labeled with a different detectable moiety, e.g. FAM dye for a forward primer and HEX dye for a reverse primer. Use of different detectable moieties is useful for discriminating between amplified products, which are of the same length or are very similar in length. Thus, in certain embodiments, at least two different fluorescent dyes are used to label different primers used in a single amplification. In still another embodiment, control primers can be labeled with one moiety, while the patient (or test sample) primers can be labeled with a different moiety, to allow for mixing of both samples (post PCR) and the simultaneous detection and comparison of signals of normal and test sample. In a modification of this embodiment, the primers used for control samples and patient samples can be switched to allow for further confirmation of results.

Analysis of amplified products from amplification reactions can be performed using an automated DNA analyzer such as an automated DNA sequencer (e.g., ABI PRISM 3100 Genetic Analyzer) which can evaluate the amplified products based on size (determined by electrophoretic mobility) and/or respective fluorescent label.

The methods and compositions provided herein provide increased sensitivity for detection of a mutated nucleic acid. Preferably the methods can detect mutated nucleic acid that is present in 10% or less, 1% or less, 0.1% or less, 0.01% or less, 0.001% or less, 0.0005% or less, 0.0003% or less, or 0.0002% or less than the total nucleic acid of a sample.

Oligonucleotides or combinations of oligonucleotides that are useful as primers or probes in the methods are also provided. These oligonucleotides are provided as substantially purified material.

Kits comprising oligonucleotides which may be primers for performing amplifications as described herein are also provided. Kits may further include oligonucleotides that may be used as probes to detect amplified nucleic acid. Kits may also include restriction enzymes for digesting BRAF wild type protein and V600 mutant proteins (e.g., V600E, but not V600K) to increase detection of BRAF V600K mutant protein by the oligonucleotide primers.

BRIEF DESCRIPTION OF THE FIGURES

FIG. 1 shows the nucleic acid sequence of the human BRAF gene corresponding to NCBI Accession number NM_004333.4 (SEQ ID NO: 1).

DETAILED DESCRIPTION

Provided herein are methods for detecting and discriminating BRAF V600 mutations, and methods for diagnosis, prognosis, management, and treatment decisions in patients with BRAF V600 mutation-related diseases or conditions. It is to be understood that methods are not limited to the particular embodiments described, and as such may vary. It is also to be understood that the terminology used herein is for the purpose of describing particular embodiments only, and is not intended to be limiting. The scope of the present technology will be limited only by the appended claims.

Provided herein are methods for detecting and discriminating BRAF mutations. The methods combine amplification of BRAF gene with nucleic acid fragmentation, such as restriction enzyme digestion, which are useful for detecting certain BRAF V600 mutations even in the presence of large amounts of other BRAF V600 mutations. Provided herein also relate to the diagnosis, prognosis, management and treatment decisions of BRAF-related disease or condition. Generally, BRAF V600 mutations are distinguished by the presence or absence of a fragmentation site, such as a restriction enzyme recognition site. By differentiating BRAF V600 mutations by a fragmentation site, the methods and diagnostics used herein can be used with various nucleic acid detection methods known in the art, such as PCR.

In some embodiments, a real-time PCR (or qPCR) assay was designed to only amplify the targeted region of the BRAF gene if the 1799T>A mutation was present. Therefore, any amplicon present in the amplification well should be enriched for the 1799T>A mutation, whether it is BRAF V600E (1799T>A) or V600K (1798-1799GT>AA) mutations.

In some embodiments, a simple restriction digest of PCR amplicons could distinguish the two BRAF mutations (i.e., V600E and V600K) by a restriction enzyme. In some embodiments, the restriction enzyme is any restriction enzyme that cuts one BRAF mutation, and not the other mutation. In some embodiments, the restriction enzyme cuts V600E mutation, but not V600K mutation. In some embodiments, the restriction enzyme cuts V600K mutation, but not V600E mutation. In some embodiments, the restriction enzyme is SfcI.

The SfcI enzyme recognizes a 6-base motif that matches the sequence of BRAF immediately upstream of the mutation site, and includes the base that is substituted in V600K but not V600E (1798G>A). Therefore, the SfcI enzyme should cut or digest the V600E mutation (and wild type, if tested on total BRAF DNA), but not the V600K mutation, which alters the enzyme recognition site. Although an amplicon enriched for the V600K mutant will provide a clearer result, even a small percentage of V600K mutation in the background of large amounts of wild type or V600E mutation should be detectable, given the correct amplicon design.

In some embodiments, the SfcI digestion consists of 1 hour incubation at 37° C., and the results can be detected with an agarose gel, in which the cut or digested V600E/wild type amplicon appears as a shorter species which therefore migrates more quickly through the gel, while the uncut or undigested V600K amplicon remains the same size as an undigested control. In some embodiments, the presence or absence of an enzyme digestion can also be detected by size separation through denaturing HPLC or through capillary electrophoresis. In some embodiments, the presence or absence of an enzyme digestion can be detected if a fluorophore-conjugated primer or a primer with detectable labels was used in the PCR amplification. A known wild type BRAF control is included to demonstrate complete enzymatic digestion, and an undigested control is included to indicate the size of uncut amplicon.

In one aspect, the present disclosure provides a method for detecting the presence of a BRAF V600E mutation in a sample of genomic DNA from a subject. In some embodiments, the subject has or is suspected of having a BRAF-related disease or condition. In some embodiments, the BRAF-related disease or condition is cancer.

In some embodiments, the method comprises amplifying BRAF genomic DNA in or from a sample from the subject using oligonucleotide primers complementary to the BRAF coding region, in order to amplify a portion of BRAF genomic DNA comprising the BRAF V600 region. In some embodiments, primers are designed to amplify BRAF coding sequences only of a 1799T>A mutation is present, in order to produce an amplification product enriched for V600E and V600K mutant sequences. In some embodiments, primers are designed to flank the V600 coding region.

In some embodiments, the BRAF amplification product is contacted with an Sfc I enzyme under conditions conducive to the enzyme cleaving its nucleic acid recognition site. According to the method, BRAF amplification products comprising wild-type sequence or a V600E (1799T>A) mutation will be digested by the Sfc I enzyme, while BRAF amplification products comprising a V600K (1798-1799GT-AA) mutation will not. Restriction enzyme digestion can be detected using methods known in the art, including, but not limited to, chromatography methods and electrophoresis methods. Accordingly, the methods described herein are useful for identifying subjects having BRAF V600 mutations and for distinguishing between the presence of BRAF V600E and BRAF V600K mutations in genomic DNA.

In one aspect, the method disclosed herein is useful generally for detecting the presence of or distinguishing a BRAF V600 mutation. In another aspect, the method is useful for diagnosing an individual with BRAF-related disease or condition.

In another aspect, the method is useful for determining a prognosis of an individual diagnosed with BRAF-related disease or condition. In another aspect, the method is useful for determining the drug sensitivity of an individual diagnosed with BRAF-related disease or condition.

In another aspect, the method is useful for guiding treatment decisions of an individual diagnosed with BRAF-related disease or condition. In another aspect, the method is useful for monitoring effectiveness of treatment of an individual diagnosed with BRAF-related disease or condition.

As used herein, the singular forms "a", "an", and "the" include plural referents unless the context clearly dictates otherwise. Thus, for example, reference to "an excipient" includes a plurality of excipients.

As used herein, the term "BRAF gene" refers generally to v-raf murine sarcoma viral oncogene homolog B1, also known in the art as NS7, BRAF1, RAFB1, and B-RAF1, including, but not limited to, human BRAF. As used herein, the term may refer to any nucleic acid encoding a BRAF protein, such as genomic DNA, mRNA, cDNA, or other engineered/recombinant nucleic acid, or portions thereof. The term encompasses, the nucleic acid sequence set forth in NCBI Accession Number NM_004333.4 (SEQ ID NO:1), as well as natural and engineered isoforms and variants. The term includes RNA transcripts corresponding to all or a portion of SEQ ID NO: 1, genomic sequences encoding SEQ ID NO:1, and all untranslated BRAF genomic sequence, such as, for example, introns, untranslated leader regions, and polyadenylation signals. Illustrative nucleic acid sequences encompassed by the term are publicly available at National Center for Biotechnology Information, Bethesda, Md. (www.ncbi.nlm.nih.gov) and HUGO Gene Nomenclature Committee, Cambridge, UK (www.genenames.org).

As used herein, the term "BRAF protein" refers generally to v-raf murine sarcoma viral oncogene homolog B1, also known in the art as NS7, BRAF1, RAFB1, and B-RAF1, including, but not limited to, human BRAF. As used herein, the term may refer to any BRAF protein, polypeptide, or a portion thereof. The term encompasses the amino acid sequence set forth in NCBI Accession Number NP_004324.2 (SEQ ID NO:2) and encoded by NCBI Accession Number NM_004333.4 (SEQ ID NO:1), as well as natural and engineered isoforms and variants.

As used herein, the term "BRAF mutant" refers generally to BRAF nucleic acid or amino acid sequences that differ from the wild-type sequence such as set forth, for example, in SEQ ID NO:1 and SEQ ID NO:2. The term includes all manner of mutation known in the art, including, but not limited to, insertions, deletions, substitutions, and inversions, encompasses both silent mutations and those that alter BRAF function, and encompasses gain-of-function and loss-of-function mutations. In some embodiments described herein, BRAF mutations comprise substitution of the valine at position 600 (V600) of SEQ ID NO:2. In some embodiments, the valine is substituted for a lysine (V600K). In some embodiments, the V600K mutation is caused by a GT to AA transversion at nucleotides 1798-1799 of the BRAF coding sequence given by NCBI Accession number NM_004333.4 (1798-1799 GT>AA). In some embodiments, the valine is substituted for a glutamic acid (V600E). In some embodiments, the V600E mutation is caused by a T to A transversion in exon 15 of the BRAF gene, at nucleotide 1799 of the coding sequence given by NCBI Accession number NM_004333.4 (1799 T>A). In some embodiments, BRAF V600 mutations comprise, glutamine (V600R), aspartic acid (V600D), alanine (V600A), and methionine (V600M) substitutions.

BRAF nucleic acid and protein sequences described herein may be isolated from any source, including, but not limited to, a human patient, a laboratory or veterinary animal (e.g., dog, pig, cow, horse, rat, mouse, etc.), a sample therefrom (e.g. tissue or body fluid, or extract thereof), or a cell therefrom (e.g., primary cell or cell line, or extract thereof).

As used herein, the term "fragmentation" refers to a process in which longer lengths of nucleic acid are broken up into shorter lengths of nucleic acid. Nucleic acids may be broken up or fragmented by chemical or biochemical means, preferably nucleic acids are fragmented in a manner that is reproducible, preferably nucleic acids are fragmented by one or more restriction endonucleases. The length of a fragment containing the nucleic acid segment of interest can depend on the length of the nucleic acid segment of interest as well as the restriction enzyme chosen to fragment the DNA.

As used herein, the term "restriction endonuclease" or "restriction enzyme" refers to an enzyme that cuts double-stranded DNA at a specific sequence (i.e., the recognition sequence or site).

As used herein, the term "sample" or "test sample" refers to any liquid or solid (or both) material can be used to test for the presence of nucleic acids. In some embodiments, a test sample is biological sample such as a cell or tissue, or a portion or fraction thereof. In some embodiments, the sample is derived from a subject having or suspected of having a BRAF-related disease or condition. In some embodiments, the BRAF-related disease or condition is cancer. In some embodiments, the subject is a human. As used herein, "sample" or "test sample" includes, but is not limited to, sputum (processed or unprocessed), bronchial alveolar lavage (BAL), bronchial wash (BW), blood, bone marrow, bodily fluids, cerebrospinal fluid (CSF), urine, plasma, serum, or tissue (e.g., biopsy material). The term "body fluid" refers to samples comprising body fluids from a subject, such as, but not limited to, sputum (processed or unprocessed), bronchial alveolar lavage (BAL), bronchial wash (BW), blood, plasma, serum, and cerebrospinal fluid (CSF). The term "patient sample" as used herein refers to a sample obtained from a human who is the subject of diagnosis, prognosis, and/or treatment of a disease.

As used herein, the term "oligonucleotide" refers to a short nucleic acid polymer composed of deoxyribonucleotides, ribonucleotides or any combination thereof. Oligonucleotides are generally between about 10, 11, 12, 13, 14 or 15 to about 150 nucleotides (nt) in length, more preferably about 10, 11, 12, 13, 14 or 15 to about 100 nt in length, more preferably about 10, 11, 12, 13, 14, or 15 to about 70 nt in length. An oligonucleotide may be used as a primer or as a probe according to methods described herein and known generally in the art.

As used herein, the term "detecting" used in context of detecting a signal from a detectable label to indicate the presence of a target nucleic acid in the sample does not require the method to provide 100% sensitivity and/or 100% specificity. A sensitivity of at least 50% is preferred, although sensitivities of at least 60%, at least 70%, at least 80%, at least 90% and at least 99% are more preferred. A specificity of at least 50% is preferred, although sensitivities of at least 60%, at least 70%, at least 80%, at least 90% and at least 99% are more preferred. Detecting also encompasses assays that produce false positives and false negatives. False negative rates may be 1%, 5%, 10%, 15%, 20% or even higher. False positive rates may be 1%, 5%, 10%, 15%, 20% or even higher.

As used herein, the term "substantially purified" in reference to oligonucleotides does not require absolute purity. Instead, it represents an indication that the specified oligonucleotide is relatively more pure than it is in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and even more preferably at least 95% pure, and most preferably at least 99% pure.

As used herein, an oligonucleotide that is "specific" for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. In some embodiments, oligonucleotides are specific for BRAF genomic sequences that flank the BRAF sequence encoding V600. In some embodiments, oligonucleotides are specific for BRAF sequences within exon 15. In some embodiments, oligonucleotides are designed to amplify a BRAF coding region only if the 1799T>A mutation is present.

The term "complement" "complementary" or "complementarity" with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the terms "amplification" and "amplify" encompass all methods for copying or reproducing a target nucleic acid sequence, thereby increasing the number of copies or amount of the nucleic acid sequence in a sample. The amplification may be exponential or linear, and the target nucleic acid may be DNA or RNA. Sequences amplified in this manner are referred to herein as an "amplicon." While illustrative methods described herein relate to amplification using the polymerase chain reaction (PCR), numerous other methods are known in the art for amplification of nucleic acids, such as, but not limited to, isothermal methods, rolling circle methods, etc. The skilled artisan will understand that these other methods may be used either in place of, or in conjunction with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-6, 858, 860 passim; Zhong, et al., Biotechniques 2001 April; 30(4):852-6, 858, 860.

A "primer" for amplification is an oligonucleotide that specifically anneals to a target nucleotide sequence and leads to addition of nucleotides to the 3' end of the primer in the presence of a DNA or RNA polymerase. As known in the art, the 3' nucleotide of the primer should generally be identical to the target sequence at a corresponding nucleotide position for optimal expression and amplification. The term "primer" as used herein includes all forms of primers that may be synthesized including, but not limited to, peptide nucleic acid primers, locked nucleic acid primers, phosphorothioate modified primers, labeled primers, and the like. In some embodiments, primers may be approximately 15-100 nucleotides in length. One of skill in the art will understand that the terms "forward primer" and "reverse primer" refer generally to primers complementary to sequences that flank the target nucleic acid.

As used herein, the term "about" when used before a numerical designation, e.g., temperature, time, amount, and concentration, including range, indicates approximations which may vary by approximately ±10%, 5%, or 1%. In some embodiments, the BRAF gene comprises one or more nucleic acid mutations at nucleotide positions 1798 and/or 1799 of SEQ ID NO:1. For example, in one embodiment, the mutation results in a BRAF protein, wherein valine 600 of SEQ ID NO:2 is changed to an amino acid other than valine, such as alanine, arginine, asparagine, aspartic acid, cysteine, glutamine, glutamic acid, glycine, histidine, isoleucine, leucine, lysine, methionine, phenylalanine, proline, serine, threonine, tryptophan, or tyrosine. In some embodiments, V600 of SEQ ID NO:2 is a changed from valine to glutamic acid (V600E) or lysine (V600K).

In some embodiments, the BRAF gene is analyzed for a V600 mutation by reverse transcribing RNA isolated from a subject so as to obtain a BRAF cDNA, amplifying the cDNA or a portion thereof comprising the nucleic acids encoding V600, and determining whether a mutation is present that would alter the identity of V600. In some embodiments, determining whether nucleic acids encoding V600 are mutated comprises contacting the amplification product with Sfc I restriction enzyme.

In some embodiments, the BRAF gene encodes a BRAF protein as shown in SEQ ID NO:2, beginning with methionine at amino acid position 1 and ending with histidine at amino acid position 766. In this embodiment, the BRAF gene begins with adenosine at nucleotide position 1 and ends with cytosine at nucleotide position 2298 of SEQ ID NO:1.

In some embodiments, the coding sequence for the mutant or wild-type BRAF protein is expressed in a mammalian cell through the use of a mammalian expression system, either inducible or constitutively, following introduction of the mammalian expression system along with the coding sequences of interest into the mammalian cell. Examples of mammalian cells include, but are not limited to, COS-7 cell, HEK-293 cell, U20S cell, and HeLa.

In some embodiments, BRAF V600 mutations are detected and distinguished using restriction enzyme digestion. BRAF genomic sequence includes a 6 base-pair Sfc I restriction site immediate upstream of the V600 coding sequence. The Sfc I site encompasses nucleotide 1798 of NCBI Accession Number NM_004333.4, but not nucleotide 1799. Thus, the site is disrupted by the V600K (1798-1799GT>AA) mutation, but not the V600E (1799T>A) mutation. According to the method, Sfc I will therefore cleave wild-type and V600E BRAF sequences at this position, but not V600K sequences. Restriction digest of BRAF nucleic acid sequences may be detected using methods known in the art, including, but not limited to, chromatography and electrophoresis.

In some embodiments, methods for detecting and distinguishing BRAF V600 mutations are provided for treating, diagnosing, providing prognosis, and/or managing a disease or condition related to a protein kinase selected from the group consisting of BRAF, a BRAF V600E mutant kinase, a BRAF V600K mutant kinase, and all other BRAF V600 mutant kinases. In some embodiments, methods for detecting and distinguishing BRAF V600 mutations are provided for treating a cancer or disease or condition related to a BRAF V600E mutant, a BRAF V600K mutant, or other BRAF V600 mutants, in conjunction with one or more therapies effective in treating the cancer or disease, including but not limited to drug therapy (e.g. chemotherapeutic drug), radiation treatment (e.g. x-ray, γ-ray, or electron, proton, neutron, or a particle beam), hyperthermia heating (e.g. microwave, ultrasound, radiofrequency ablation), vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow or stem cell transplantation.

In some embodiments, methods for detecting and identifying BRAF V600 mutations are provided for treating BRAF V600E, BRAF V600K or other BRAF V600 mutations related disease or condition or cancer in a subject by administering to the subject an effective amount of a composition including one or more suitable chemotherapeutic agents. In some embodiments, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib.

In some embodiments, kits for detecting and identifying BRAF V600 mutations (e.g., V600E, V600K) are described. In some embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a protein kinase mediated disease or condition; the invention kit includes written instructions for use and/or other indication that the composition is suitable or approved for administration to a mammal, e.g., a human, for a protein kinase-related disease or condition; and the composition is packaged in unit dose or single dose form, e.g., single dose pills, capsules, or the like.

In some embodiments, methods for detecting and identifying BRAF V600 mutations are used for diagnosis, prognosis, management, and treatment decisions of a BRAF or BRAF V600 mutations-related (e.g., V600E, V600K) disease or condition, selected from the group consisting of melanoma, colorectal cancer, thyroid cancer, NSCLC, and adenocarcinomas. In some embodiments, the disease or condition is selected from the group consisting of neurologic diseases such as ischemic stroke, multi-infarct dementia, head injury, spinal cord injury, Alzheimer's disease (AD), Parkinson's disease; neoplastic diseases including, but not limited to, glioma, sarcoma, carcinoma (e.g. lung, breast, pancreatic, renal), lymphoma (e.g. histiocytic lymphoma) and cancer of the liver, breast, and ovary, neurofibromatosis, myelodysplastic syndrome, leukemia, tumor angiogenesis; pain of neuropathic or inflammatory origin, including acute pain, chronic pain, and migraine; cardiovascular diseases including heart failure, cardiac hypertrophy, thrombosis (e.g. thrombotic microangiopathy syndromes), atherosclerosis, reperfusion injury; inflammation including, but not limited to, psoriasis, polycystic kidney disease (PKD), arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, organ transplant rejection, graft versus host disease; renal or prostatic diseases including diabetic nephropathy, nephrosclerosis, glomerulonephritis, prostate hyperplasia; metabolic disorders, obesity; infection, including, but not limited to *Helicobacter pylori* and Influenza virus, fever, sepsis; pulmonary diseases including chronic obstructive pulmonary disease (COPD) and acute respiratory distress syndrome (ARDS); genetic developmental diseases such as Noonan's syndrome, Costello syndrome, (faciocutaneoskeletal syndrome), leopard syndrome, cardio-faciocutaneous syndrome (CFC), and neural crest syndrome abnormalities causing cardiovascular, skeletal, intestinal, skin, hair and endocrine diseases.

In some embodiments, the method comprises administering an agent that binds the BRAF V600E mutation, but not other BRAF V600 mutations (e.g., V600K) or the wild type BRAF protein of a subject suffering from BRAF V600E-related disease or condition and thereby treating the subject suffering from BRAF V600E-related disease or condition. In some embodiments, the agent renders BRAF V600E mutant protein inactive. In some embodiments, the agent specifically targets BRAF V600E mutant protein.

In some embodiments, the agent that binds the BRAF V600E protein is a BRAF inhibitor. Examples of suitable BRAF inhibitors include but are not limited to GDC-0879, PLX4720, PLX4032 (also known as N-(3-(5-(4-chlorophenyl)-1H-pyrrolo[2,3-b]pyridine-3-carbonyl)-2,4-difluorophenyl)propane-1-sulfonamide) (Plexxikon, Inc., Berkeley, Calif.; (24)), RAF265 (also known as 1-methyl-5-(2-(4-(trifluoromethyl)-1H-imidazol-2-yl)pyridin-4-yloxy)-N-(4-(trifluoromethyl)phenyl)-1H-benzo[d]imidazol-2-amine) (CHIR-265; Novartis Pharmaceuticals, Basel, Switzerland), Sorafenib (also known as 4-[4-[[4-chloro-3-(trifluoromethyl)phenyl]carbamoylamino]phenoxy]-N-methyl-pyridine-2-carboxamide) (BAY43-9006; Bayer, Pittsburgh, Pa.), XL281 (Exelixis, San Francisco, Calif.), SB-590885 (also known as 5-[2-[4-[2-(Dimethylamino) ethoxy]phenyl]-5-(4-pyridinyl)-1H-imidazol-4-yl]-2,3-dihydro-1H-inden-1-one-oxime) (SmithKline Beecham, Philadelphia, Pa.), and PLX4720 (also known as N-(3-(5-chloro-1H-pyrrolo[2,3-b]pyridine-3-carbonyl)-2,4-difluorophenyl)propane-1-sulfonamide) (Plexxikon, Inc., Berkeley, Calif.).

In some embodiments, the method for treating a subject suffering from BRAF V600E-related disease or condition comprises administering a molecule that targets the BRAF V600E mutant or transcripts thereof in the subject and thereby treating the subject suffering from BRAF V600E-related disease or condition.

In some embodiments, the molecule that targets the BRAF V600E mutant or transcripts thereof may be a nucleic acid molecule. For example, the nucleic acid molecule may be a RNA molecule such as a siRNA molecule. In one embodiment, the siRNA molecule is directed to the BRAF V600E mutant sequence.

In some embodiments, the methods, diagnostics, and kits provided herein are used for detecting the BRAF V600E, V600K, and other V600 mutations in different cell types and can be used for the diagnosis of different cancers, such as, but not limited to, melanoma, colorectal cancer, lung cancer and thyroid cancer. The method provided herein addresses the need for a rapid, non-invasive, and accurate screening assay for detecting and distinguishing BRAF V600E and V600K mutations, and identifies patients who need to be treated with more aggressive treatment regimens. The methods provided herein may be useful as a predictor of outcome for cancer patients.

As a non-limiting example, the methods provided herein may be used to manage or formulate treatment decision for patients with advanced, metastatic melanoma. These patients are at the highest risk for disease progression, and early detection of an increase in disease activity would lead to earlier treatment and improvement in outcome. The methods provided herein may also be directed to testing patients with earlier stages of disease, who are at risk for metastatic spread of their disease. Early intervention with additional diagnostic tests and treatments would lead to improved patient survival.

In some embodiments, the methods provided herein may be useful to predict and/or confirm pathologic features of metastatic melanoma associated with BRAF V600E and V600K mutations. The site of primary melanoma associated with various BRAF mutations may be different. Metastatic melanoma with BRAF V600E mutation has more primary melanoma on the extremities, whereas V600K mutation has more primary melanoma in the head and neck region. The effect of cumulative sun-induced damage (CSD) may be different. Metastatic melanoma with BRAF V600E mutation has little or no CSD scores, whereas V600K mutation has high scores of CSD. The age at diagnosis of metastatic melanoma may vary. Metastatic melanoma with BRAF V600E mutation occurs more frequently in younger people, whereas V600K mutation occurs more frequently in older people. The disease-free interval (DFI) may also vary. Metastatic melanoma with BRAF V600E mutation has a longer DFI, whereas V600K mutation has a shorter DFI. Considering the differences of the site of primary melanoma, CSD, age, and DFI associated with BRAF V600E and V600K mutation-related metastatic melanoma, early detection and identification of BRAF V600E and V600K mutations would lead to appropriate and specific treatment for each V600 mutation and improvement in patient survival.

In some embodiments, a method of identifying or screening molecules that bind or block the BRAF V600K mutations, but not BRAF wild type or other BRAF V600 mutations (e.g., V600E) involves contacting a molecule of interest with a sample taken from a subject suffering from BRAF V600K-related disease or condition, and determining whether the molecule of interest alters BRAF V600K mutant protein activity. Alteration of the BRAF V600K mutant protein activity is indicative that the molecule of interest binds or blocks the BRAF V600K mutant protein in the sample.

For the methods provided herein, a single primer could be used for detection, for example as in single nucleotide primer extension, or a second primer can be used which can be upstream or downstream of the mutation specific primer. One or more of the primers used may be mutation specific primers. Preferably, the mutation specific primer contains wild-type sequence, more preferably at least about 3-40 consecutive nucleotides of wild-type sequence.

One of skill in the art will recognize that a restriction enzyme fragmentation/digestion method can be modified by using a restriction enzyme that cuts at a particular frequency or a particular site, or by using multiple restriction enzymes. The choice of enzyme or enzyme combinations is chosen to suit the target of interest in an assay. Enzymes can be chosen using a restriction enzyme map of the region of interest, which may be readily generated using software programs well-known in the art.

Chemical fragmentation may include degradation by a nuclease such as DNase or RNase which generate fragments having 3'-OH, 5'-OH, 3'-phosphate and 5'-phosphate ends; depurination or depyrimidation with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations (see, for example, U.S. Pat. No. 6,495,320). It is possible to depurinate or depyrimidinate the DNA, which is then fragmented in the presence of a base (i.e., "β-elimination"). DNA can be fragmented by oxidation, alkylation or free radical addition mechanisms. Metal cations, which are often combined with organic molecules which may function as chemical catalysts, for example imidazole, are used for fragmenting RNA. This fragmentation is preferably carried out in an alkaline medium and generates fragments having 3'-phosphate ends. Chemical catalysts that may be used for nucleic acid fragmentation include MOPS, HEPES, PIPES, and bioorganic polyamines, such as spermine, spermidine and putrescine (Bibille et al., 27 Nucleic Acids Res. 3931-3937 (1999)).

Different nucleic acid fragmentation techniques have been described, for example, in Trawick et al., 98 Chem Rev. 939-960 (1998), Oivanen at al., 1998, 98 Chem Rev. 961-990 (1998) and Laayoon, et al. U.S. Pat. No. 6,902,891. A method for fragmenting and labeling RNA is described in WO88/04300A1, in which fragmentation is carried out using RNA which possesses enzymatic properties (ribozymes).

Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-related hydrolysis. See for example, Sambrook et al., "Molecular Cloning: A Laboratory Manual," 3rd Ed. Cold Spring Harbor Laboratory Press, Cold Spring Harbor, N.Y. (2001).

Preferential cleavage can be achieved by other methods known in the art such as the Maxam-Gilbert method. This method involves degrading DNA at a specific base using chemical reagents. A. M. Maxim et al., 65(1) Meth. in Enzym. 499-560 (1980). In general, this method starts with end labeled DNA and cleaves by base specific reagents. For example with guanine bases (the same principle applies to all four bases), DNA of interest is end-labeled (can be 5'- or 3'-end labeling). Then one kind of base is modified, for example with dimethyl sulfate (DMS) to methylate guanines. Conditions can be adjusted to achieve various frequencies of methylation. Following methylation. a reagent such as piperidine is added which causes loss of a methylated base and then breaks the DNA backbone at the site of the lost base (the apurinic site).

In some embodiments, the method can be applied to any type of tissue from a patient. Sources of such tissue include but are not limited to nervous system, thyroid, skin, gastrointestinal tract, large intestine, biliary tract, ovary, eye, prostate, central nervous system, liver, small intestine, breast, pancreas, soft tissue, digestive tract, adrenal gland, autonomic ganglia, hematopoietic and lymphoid tissue, lung, esophagus, pituitary, and stomach.

In some embodiments, the methods can be applied over a wide range of tumor types. This allows for the preparation of individual tumor expression profiles whereby expression levels of BRAF V600 mutant sequences (e.g., V600E, V600K) are determined in individual patient samples and response to various BRAF inhibitors is predicted. In some embodiments, the methods of the invention are applied to melanoma tumors or metastatic melanoma.

In some embodiments, the method comprises obtaining a sample of a tissue or a body fluid from the subject (e.g., a mammal) wherein the sample contains nucleic acid. Non-limiting examples of tissue or body fluids that can be used include blood, plasma, lymph, tumor biopsies, and body tissue. In some embodiments, the tissue sample comprises paraffin embedded tissue specimens. The method may be performed using any sample containing nucleic acid. In some embodiments, the nucleic acid is deoxyribonucleic acid (DNA). In some embodiments, the nucleic acid is ribonucleic acid (RNA).

Samples may be obtained by standard procedures and may be used immediately or stored (e.g., the sample may be frozen between about −15° C. to about −100° C.) for later use. Samples may be obtained from patients suspected of having a mutated nucleic acid sequence, for example from a tumor cell or cancer cells. The presence of mutated nucleic acids in a sample can be determined by amplifying cancer marker regions. Thus, any liquid or solid material believed to contain cancer marker nucleic acids can be an appropriate sample.

The sample may be processed to release or otherwise make available a nucleic acid for detection as described herein. Such processing may include steps of nucleic acid manipulation, e.g., preparing a cDNA by reverse transcription of RNA from the biological sample. Thus, the nucleic acid to be amplified by the methods of the invention may be genomic DNA, cDNA, single stranded DNA or mRNA.

In some embodiments, methods of DNA isolation known to those skilled in the art are utilized. In general, the aim is to separate DNA present in the nucleus of the cell from other cellular components. The isolation of DNA usually begins with lysis of tissue or cells. This process is essential for the destruction of protein structures and allows for release of nucleic acids from the nucleus. Lysis is carried out in a salt solution, containing detergents to denature proteins or proteases (enzymes digesting proteins), such as Proteinase K, or in some cases both. It results in the breakdown of cells and dissolving of membranes. Methods of DNA isolation include, but are not limited to, phenol:chloroform extraction, high salt precipitation, alkaline denaturation, ion exchange column chromatography, resin binding, and paramagnetic bead binding.

Methods of RNA isolation known to those skilled in the art are also utilized. RNA may be isolated and prepared for hybridization by a variety of methods including, but not limited to, Trizol® and Guanidinium thiocyanate-phenol-chloroform extraction. The principle of RNA isolation is based on cell/tissue lysis, followed by extraction, precipitation, and washing.

Thermal and isothermal amplification methods including, but not limited to, polymerase chain reaction (PCR), real-time PCR (qPCR), reverse transcriptase polymerase chain reaction (RT-PCR), ligase chain reaction (LCR), helicase dependent amplification (HDA) and Nucleic Acid Sequence Based Amplification (NASBA) and Amplification Refractory Mutation System (ARMS) can also be utilized.

Methods involving labeling primers used during the amplification step can be utilized such that the amplification products are labeled with a detectable marker and hybridizing the amplification product to oligonucleotide probes labeled with a detectable marker. Detectable markers include but are not limited to luminescent tags, fluorescent tags, and radioactive tags. Labeled amplification product can be directly measured using methods corresponding to the type of label used according to methods would be known to one skilled in the art. Labeled probe can be hybridized to the amplification product according to methods known to one skilled in the art.

Nucleic acid samples or isolated nucleic acids may be amplified by various methods known to the skilled artisan. PCR is used to amplify mutated nucleic acids of interest. In this method, two or more oligonucleotide primers that flank or include, and anneal to opposite strands of a nucleic acid of interest are repetitively annealed to their complementary sequences, extended by a DNA polymerase (e.g., AmpliTaq Gold polymerase), and heat denatured, resulting in exponential amplification of the target nucleic acid sequences. Cycling parameters can be varied, depending on the length of nucleic acids to be extended. The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill. For example, the length of a short nucleic acid or oligonucleotide can relate to its hybridization specificity or selectivity.

Assay controls may be used in the assay for detecting a mutated nucleic acid sequence. An internal positive amplification control can be included in the sample, utilizing oligonucleotide primers and/or probes.

In some embodiments, sequences from two or more regions of interest are amplified in the same reaction vessel. In this case, the amplicon(s) could be detected by first size-separating the amplicons then detection of the size-separated amplicons. The separation of amplicons of different sizes can be accomplished by, for example, gel electrophoresis, column chromatography, denaturing HPLC, capillary electrophoresis, hybridization with a probe, or sequencing. These and other separation methods are well-known in the art. In one example, amplicons of about 10 to about 150 base pairs whose sizes differ by 10 or more base pairs can be separated, for example, on a 4% to 5% agarose gel, (a 2% to 3% agarose gel for about 150 to about 300 base pair amplicons) or a 6% to 10% polyacrylamide gel. The separated nucleic acids can then be stained with a dye such as ethidium bromide and the size of the resulting stained band or bands can be compared to a standard DNA ladder.

In some embodiments, amplified nucleic acids are detected by hybridization with a mutation-specific probe. Probe oligonucleotides, complementary to a portion of the amplified target sequence may be used to detect amplified fragments. Amplified nucleic acids for each of the target sequences may be detected simultaneously (i.e., in the same reaction vessel) or individually (i.e., in separate reaction vessels). In some embodiments, the amplified DNA is detected simultaneously, using two distinguishably-labeled, gene-specific oligonucleotide probes, one which hybridizes to the first target sequence and one which hybridizes to the second target sequence.

The probe may be detectably labeled by methods known in the art. Useful labels include, e.g., fluorescent dyes (e.g., Cy5®, Cy3®, FITC, rhodamine, lanthamide phosphors, Texas red), 32P, 35S, 3H, 14C, 125I, 131I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected. For example, detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, e.g., Cy3® or Cy5® and then incorporated into genomic nucleic acids during nucleic acid synthesis or amplification. Nucleic acids can thereby be labeled when synthesized using Cy3®- or Cy5®-dCTP conjugates mixed with unlabeled dCTP. The label can be attached by spacer arms of various lengths to reduce potential steric hindrance or impact on other useful or desired properties. See, e.g., Mansfield, 9 *Mol. Cell. Probes* 145-156 (1995).

A probe oligonucleotide, complementary to the amplified region of nucleic acid, is used to detect the amplification of mutated nucleic acids. The probe may be detectably labeled by methods known in the art. The binding of a probe to the amplified region of the mutated nucleic acid may be determined by hybridization as is well known in the art. Hybridization may be detected in real time or in non-real time.

One general method for real time PCR uses fluorescent probes such as the TaqMan® probes, molecular beacons and scorpions. Real-time reverse-transcriptase (RT) PCR quantitates the initial amount of the template with more specificity, sensitivity and reproducibility, than other forms of quantitative reverse transcriptase PCR, which detect the amount of final amplified product. Real-time RT-PCR does not detect the size of the amplicon. The probes employed in TaqMan® and molecular beacon technologies are based on the principle of fluorescence quenching and involve a donor fluorophore and a quenching moiety.

In some embodiments, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore).

Other fluorescent nucleotide analogs can be used. See, e.g., Jameson, 278 Meth. Enzymol. 363-390 (1997); Zhu, 22 Nucl. Acids Res. 3418-3422 (1994). U.S. Pat. Nos. 5,652, 099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135, 717 describes phthalocyanine and tetrabenztriazaporphyrin reagents for use as fluorescent labels.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides. See, e.g., Henegariu, 18 Nat. Biotechnol. 345-348 (2000).

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulphur containing side chains of amino acids. See, e.g., U.S. Pat. Nos. 5,580,990; 5,714,327; and 5,985, 566; and European Patent No. 0539466.

The binding of a probe to the marker sequence flanking the tandem repeat region may be determined by hybridization as is well known in the art. Hybridization may be detected in real time or in non-real time.

Nucleic acid amplification may be done using real-time PCR methods, such as, for example, TaqMan® methods. Probes and amplification methods suitable for TaqMan® methods are known and readily available in the art.

In some embodiments, real time PCR (or qPCR or quantitative polymerase chain reaction) is performed using TaqMan® probes in combination with a suitable amplification/analyzer such as the ABI Prism 7900HT Sequence Detection System. The ABI PRISM® 7900HT Sequence Detection System is a high-throughput real-time PCR system that detects and quantitates nucleic acid sequences. Briefly, TaqMan® probes specific for each allele are included in the PCR assay. These probes contain a reporter dye at the 5' end and a quencher dye at the 3' end. Each allele specific probe is conjugated with a different fluorescent reporter dye. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation.

Real Time detection on the ABI Prism 7900HT or 7900HT Sequence Detector monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

To minimize the potential for cross contamination, reagent and mastermix preparation, specimen processing and PCR setup, and amplification and detection are all carried out in physically separated areas. In addition, Uracil-N-Glycosylase is utilized (along with the incorporation of Uracil into PCR amplicons) to eliminate carry over contamination.

The following examples serve to illustrate the present invention. These examples are in no way intended to limit the scope of the invention.

EXAMPLE 1

Distinguishing BRAF V600K from V600E Mutations

This example demonstrates the detection and distinction of BRAF V600E and BRAF V600K mutations according to select embodiments described herein.

A sensitive quantitative PCR (qPCR) assay was used to amplify BRAF coding sequences encoding all or a portion of V600 from DNA present in the plasma of melanoma patients and from control samples. Patient samples and DNAs were prepared using methods known in the art. Primers were designed to selectively produce amplification products if the 1799T>A mutation was present. Such primers amplify both V600E (1799T>A) and V600K (1798-1799GT>AA) mutations, producing an amplicon product enriched for these mutant sequences. Illustrative amplification conditions are as follows: about 25 ng of DNA is amplified in a total reaction volume of 25 µL mastermix (containing PCR buffer, forward and reverse primers, probe, and polymerase), beginning with a 10-minute polymerase-activating incubation at 95° C., followed by 5 "pre-amplification" cycles of (95° C.-20 sec.; 58° C.-60 sec.), followed by 50 cycles of (95° C.-30 sec.; 60° C.-60 sec.).

The presence of V600E and V600K mutations in the amplicon was distinguished by digestion of the amplicon with Sfc I, the recognition site for which is disrupted in V600K mutants, but not V600E mutants. According to the method, Sfc I will therefore cleave wild-type and V600E BRAF sequences at this position, but not V600K sequences.

The SfcI digestion was accomplished using standard conditions, typically 1 hour incubation at 37° C. Restriction digest of BRAF nucleic acid sequences was detected by gel electrophoresis, but may be detected using methods known in the art, including, but not limited to, chromatography and electrophoresis. The presence of V600E sequences in the amplicon was evident by the generation of Sfc I restriction products of an appropriate size. The presence of V600K sequences in the amplicon was evident from the presence of full-length amplicon sequences in the digested sample.

Figure 2:
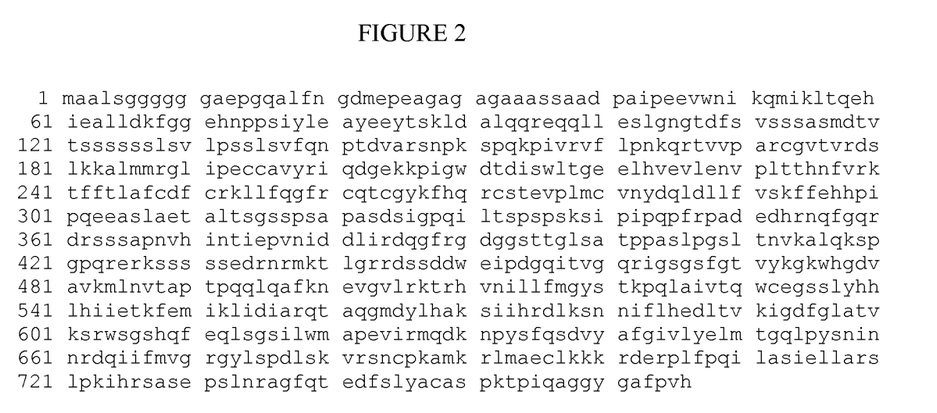
FIG. 2 shows the amino acid sequence of the human BRAF protein corresponding to NCBI Accession number NP_004324.2 (SEQ ID NO:2).
Figure 3:
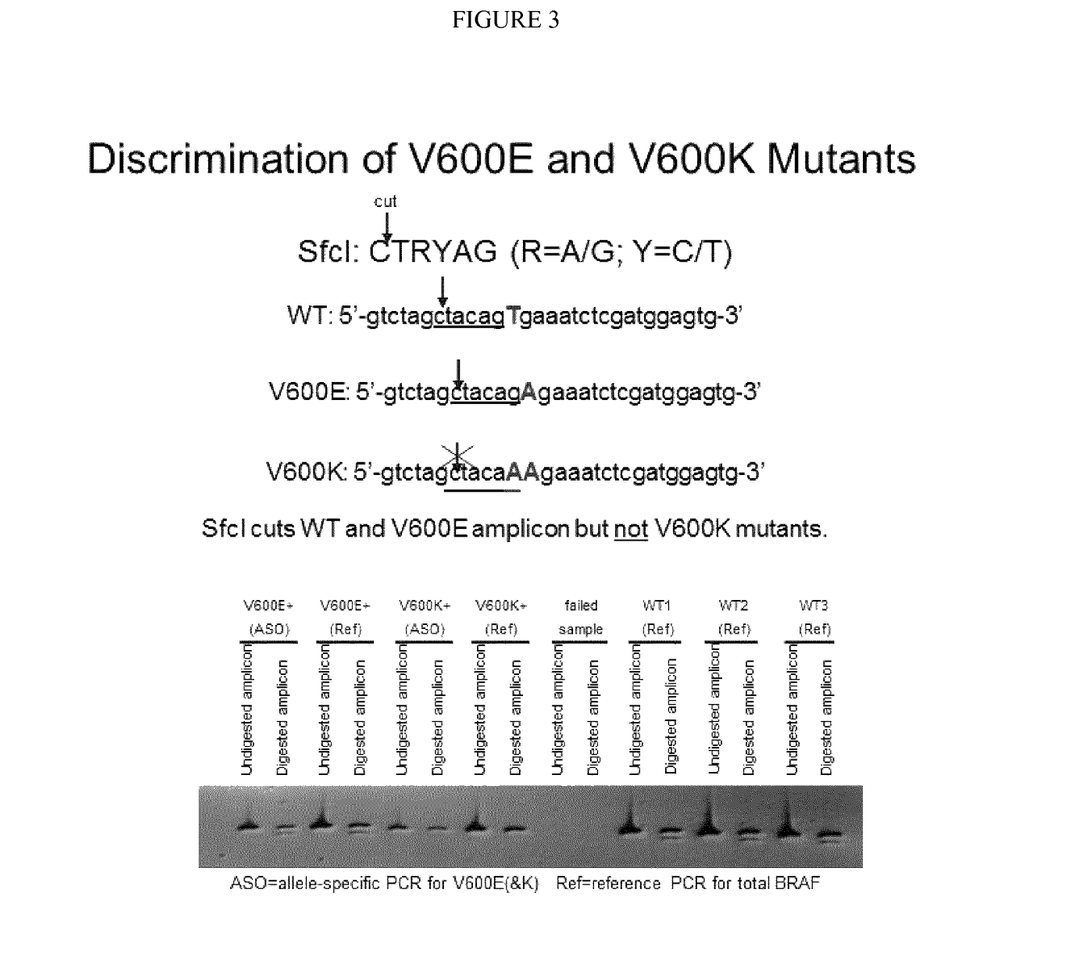
FIG. 3 shows the discrimination of V600E and V600K BRAF mutants according to the methods described herein. Wild-type (SEQ ID NO: 3), V600E (SEQ ID NO: 4), and V600K (SEQ ID NO: 5) BRAF sequences were amplified, digested with SfcI, and analyzed by gel electrophoresis. According to the methods described herein, SfcI cuts the wild-type and V600E sequences, generating a restriction fragment doublet, but does not cut the V600K sequence.

Results are shown in FIG. 3. The data show that the method distinguishes between the presence of BRAF V600E and V600K mutations in patient samples with little background resulting from the presence of wild-type BRAF sequences. These results demonstrate that the technology described herein is useful in methods comprising detecting and/or distinguishing between BRAF V600E and V600K mutations, such as methods for diagnosis, prognosis, or treatment of BRAF-related diseases or conditions.

EXAMPLE 2

BRAF Inhibitors

Eligible patients with either BRAF V600E or V600K mutant melanoma are enrolled in clinical trials of BRAF inhibitors. Clinical and pathologic features associated with BRAF V600E and V600K mutations are accessed. The effect of BRAF inhibitors on patients with BRAF V600E and V600K mutations are examined. Survival analysis is carried out to determine statistical significance. P values less than 0.05 were considered statistically significant.

A BRAF inhibitor is identified as predominately inhibits BRAF V600K mutation, and not V600E mutation, when patients with BRAF V600K mutant melanoma survive significant longer than patients with BRAF V600E mutant melanoma under the BRAF inhibitor treatment.

EXAMPLE 3

Kinase Activity Assays

Kinase activity assays can be used to identify or screen molecules that bind or block specific BRAF mutant protein by contacting a molecule of interest with a sample taken from a subject suffering from specific BRAF mutation-related disease or condition, and determining whether the molecule of interest alters BRAF mutant protein activity, alteration of the specific BRAF mutant protein activity being indicative that the molecule of interest binds or blocks the specific BRAF mutant protein in the sample. For example, kinase activity assays can be used to identify or screen inhibitors that specifically bind or block BRAF V600K mutant protein by contacting an inhibitor with a sample taken from a patient suffering from BRAF V600K-related metastatic melanoma. The inhibitor can be determined as effective and specific for BRAF V600 mutation if it alters V600K mutant protein activity, but not wild type or V600E mutant protein activity.

The effect of potential modulators of kinase activity of a BRAF mutation can be measured in a variety of different assays known in the art. For example, direct radiometric, indirect FRET or AlphaScreen assays may be used to assess the level of phosphorylation of a substrate in the presence of test compounds in order to determine the inhibitory affect of the compound on the kinase. Invitrogen (Carlsbad, Calif.) uses a FRET based assay for Btk, EGFR, EphB2, Flt3, Irak4, Kdr, MAP2K1, MAPKAPK2, PDGFRB, PKC theta, Stk6 and Yes. For these assays, compounds of the invention were screened by Invitrogen using Z'-Lyte™ kinase assay.

Invitrogen kinase assay involves use of a specific peptide substrate optimized for each kinase, containing a fluorophore at each end that make up the FRET pair. The peptide sensitivity to proteolytic cleavage depends on phosphorylation of the peptide. Non-phosphorylated peptide is cleaved by a protease while peptide phosphorylated by the kinase is not cleaved. Cleavage of the peptide disrupts the FRET between the donor (coumarin) and acceptor (fluorescein) fluorophores, resulting in an increase in the ratio of donor emission to acceptor emission. The emission ratio of coumarin to fluorescein is used to assess the reaction progress. The extent of phosphorylation is determined from the emission ratio, which is low when the kinase is active (phosphorylated peptide is not cleaved, FRET pair connected) or higher for inhibited kinase (non-phosphorylated peptide is cleaved, FRET pair separated). Thus, the assay involves a kinase reaction in the presence of varying concentrations of a given compound, a development reaction with site specific protease, and detection of the fluorescent emission ratio of coumarin and fluorescein. The emission ratio as a function of compound concentration was used to determine the $IC_{50}$ value. Reaction conditions for each kinase are determined to provide optimal reaction times, incubation temperature, kinase and ATP concentrations. Test samples are made up in 1× kinase buffer (50 mM HEPES pH 7.5, 50 mM $MgCl_2$, 5 mM EGTA, 0.05% BRIJ-35) and compound at desired concentration prepared in DMSO such that the final DMSO is 1%. Assay controls include 0% phosphorylation, which contains no ATP, 100% phosphorylation control, which consists of a synthetically phosphorylated peptide, and 0% inhibition control, which contains active kinase conditions without compound. Typically, assay plates are prepared to 10 μl final volume per sample, adding 2.5 μl of compound at 4× the desired concentration in 4% DMSO (serial dilution of compound provides concentration curve), 5 μl of the desired kinase mixed with Z'-LYTE™ peptide substrate (2× in 2× kinase buffer, final peptide at 2 μM), and 2.5 μl of 4×ATP solution. All kinase except for MAP2K1 were at 10 μM ATP in the kinase reaction, while MAP2K1 was at 100 μM. Samples are mixed and the kinase reaction is incubated 1 hour at room temperature, after which 5 μl of development solution is added and mixed. After incubation for another 1 hour at room temperature, 5 μl of stop reagent is added to each sample and mixed. The fluorescence signals are measured to determine the emission ratio.

AlphaScreen assay was used to screen kinases. The assay is similarly dependent on the phosphorylation of a peptide substrate. In this assay, an antibody that recognizes phosphorylated substrate is bound to an acceptor bead. The peptide substrate is attached to biotin, which binds to a donor bead that contains streptavidin. Thus phosphorylated substrate is bound by antibody and streptavidin, bringing the donor and acceptor beads into close proximity when kinase is not inhibited. The donor produces singlet oxygen, which results in emission from the acceptor when they are in close proximity. Conversely, when kinase is inhibited, the donor and acceptor beads are not associated and the emission from the acceptor is reduced. The fluorescence signal vs. compound concentration was used to determine the $IC_{50}$ values.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that the materials, methods, and examples provided here are representative of some embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for identifying a BRAF mutation in a biological sample, the method comprising:
   (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, wherein the primers amplify both a V600E (1799T>A) mutation and a V600K (1798-1799GT>AA) mutation in the BRAF gene and do not amplify the wild type BRAF gene;
   (b) subjecting the amplicons to a restriction enzyme digestion; and
   (c) identifying a BRAF V600E mutation (1799T>A) in the sample if a digestion product is detected, or identifying a BRAF V600K mutation (1798-1799GT>AA) in the sample if a product of the restriction enzyme digestion is not detected.

2. The method of claim 1, wherein the amplicon comprises the BRAF V600E mutation (1799T>A).

3. The method of claim 1, wherein the amplicon comprises the BRAF V600K mutation (1798_1799GT>AA).

4. The method of claim 1, wherein the restriction enzyme recognizes a 6-base motif that matches the sequence of the BRAF gene immediately upstream of the thymidine (T) to adenosine (A) mutation at position 1799 of the BRAF gene.

5. The method of claim 1, wherein the sample DNA is extracted from the plasma of an individual.

6. The method of claim 1, wherein the individual is a melanoma patient.

7. The method of claim 1, wherein the incubation for the restriction enzyme digestion is for about one hour incubation at about 37° C.

8. The method of claim 1, wherein the restriction enzyme is SfcI.

9. The method of claim 1, further comprising (c) subjecting the digested amplicon to size separation.

10. The method of claim 9, wherein size separation comprises denaturing HPLC.

11. The method of claim 9, wherein size separation comprises gel electrophoresis or capillary electrophoresis.

12. The method of claim 11, wherein the capillary electrophoresis comprises utilizing a fluorophore-conjugated primer in the PCR amplification.

13. A method for determining the drug sensitivity of an individual diagnosed with a BRAF-related disease or condition by determining if the individual has a specific mutation in the BRAF gene associated with a BRAF-related disease or condition comprising:
   (a) amplifying a sample DNA from an individual by PCR utilizing a forward primer and a reverse primer, wherein the forward primer and the reverse primer are configured to amplify DNA sequences containing a thymidine (T) to adenosine (A) mutation at position 1799 of the BRAF gene, wherein the primers do not amplify the wild type BRAF gene;
   (b) subjecting the amplicon to a restriction enzyme digestion with SfcI; and
   (c) determining that the individual is likely to respond to trametinib when a restriction enzyme digestion product is detected in the sample, or determining that the individual is likely to respond to vemurafenib or trametinib if a restriction enzyme digestion product is not detected in the sample.

* * * * *